(12) United States Patent
Hong et al.

(10) Patent No.: US 10,900,969 B2
(45) Date of Patent: Jan. 26, 2021

(54) BIOMIMETIC MICROFLUID DEVICE FOR CAPTURING CIRCULATING TUMOR CELLS

(71) Applicant: THE BOARD OF TRUSTEES OF THE UNIVERSITY OF ILLINOIS, Urbana, IL (US)

(72) Inventors: Seungpyo Hong, Naperville, IL (US); Ja Hye Myung, Daejeon (KR)

(73) Assignee: UNIVERSITY OF ILLINOIS CHICAGO, Chicago, IL (US)

( * ) Notice: Subject to any disclaimer, the term of this patent is extended or adjusted under 35 U.S.C. 154(b) by 656 days.

(21) Appl. No.: 15/123,156

(22) PCT Filed: Mar. 9, 2015

(86) PCT No.: PCT/US2015/019466
§ 371 (c)(1),
(2) Date: Sep. 1, 2016

(87) PCT Pub. No.: WO2015/134972
PCT Pub. Date: Sep. 11, 2015

(65) Prior Publication Data
US 2017/0168063 A1    Jun. 15, 2017

Related U.S. Application Data

(60) Provisional application No. 61/949,472, filed on Mar. 7, 2014.

(51) Int. Cl.
*G01N 33/543* (2006.01)
*G01N 33/574* (2006.01)
*B01L 3/00* (2006.01)

(52) U.S. Cl.
CPC ...... *G01N 33/57492* (2013.01); *B01L 3/5027* (2013.01); *G01N 33/543* (2013.01);
(Continued)

(58) Field of Classification Search
None
See application file for complete search history.

(56) References Cited

U.S. PATENT DOCUMENTS 5,395,609 A   3/1995 Stuttle
5,460,945 A   10/1995 Springer et al.
(Continued)

FOREIGN PATENT DOCUMENTS

CN   101583722 A   11/2009
CN   101918543 A   12/2010
(Continued)

OTHER PUBLICATIONS

Burdick et al., Expression of E-selectin ligands on circulating tumor cells: Cross-regulation with cancer stem cell regulatory pathway? *Front. Oncol.* 2: 103 (2012).
(Continued)

*Primary Examiner* — Christopher L Chin
(74) *Attorney, Agent, or Firm* — Marshall, Gerstein & Borun LLP

(57) ABSTRACT

A method of capturing a Circulating Tumor Cell (CTC) and Circulating Cancer Cells (CSC) from a sample includes introducing a sample into a flow based multichannel device having a cell capture surface and a flow modification surface under conditions that allow a CTC to bind to a cell rolling-inducing agent and a capturing agent disposed on the cell capture surface. The invention also provides for flow based multichannel devices to capture CTCs and CSCs from a sample.

20 Claims, 12 Drawing Sheets

(52) U.S. Cl.
CPC .......... *B01L 2300/0636* (2013.01); *B01L 2300/0654* (2013.01); *B01L 2300/0816* (2013.01); *B01L 2300/0861* (2013.01); *B01L 2300/0877* (2013.01)

(56) References Cited

U.S. PATENT DOCUMENTS

| | | | |
|---|---|---|---|
| 5,939,404 | A | 8/1999 | Iijima et al. |
| 6,551,843 | B1 | 4/2003 | Rao et al. |
| 6,773,928 | B1 | 8/2004 | Yin et al. |
| 9,964,541 | B2* | 5/2018 | Hong .......... G01N 33/574 |
| 2003/0087292 | A1 | 5/2003 | Chen et al. |
| 2007/0017633 | A1 | 1/2007 | Tonkovich et al. |
| 2007/0026417 | A1 | 2/2007 | Fuchs et al. |
| 2007/0041934 | A1 | 2/2007 | William et al. |
| 2007/0178084 | A1 | 8/2007 | King et al. |
| 2008/0124721 | A1 | 5/2008 | Fuchs et al. |
| 2008/0199362 | A1 | 8/2008 | Chong et al. |
| 2008/0206757 | A1 | 8/2008 | Lin et al. |
| 2012/0077246 | A1 | 3/2012 | Hong et al. |
| 2013/0309707 | A1 | 11/2013 | Bersano-Begey et al. |
| 2017/0254809 | A1* | 9/2017 | Hong .......... G01N 33/574 |

FOREIGN PATENT DOCUMENTS

| | | |
|---|---|---|
| CN | 102414562 A | 4/2012 |
| EP | 02594942 A1 | 5/2013 |
| JP | 2012-520687 A | 9/2012 |
| WO | WO-2008/089270 A2 | 7/2008 |
| WO | WO-2008131301 A1 | 10/2008 |
| WO | WO-2009043057 A2 | 4/2009 |
| WO | WO-2010/108003 A2 | 9/2010 |
| WO | WO-2010/111388 A2 | 9/2010 |
| WO | WO-2010/124227 A2 | 10/2010 |
| WO | WO-2015/134972 A2 | 9/2015 |

OTHER PUBLICATIONS

Hughes et al., Nanobiotechnology for the capture and manipulation of circulating tumor cells. Wiley Interdiscip. *Rev. Nanomed. Nanobiotechnol.* 4(3): 291-309 (2012).
Hughes et al., Microtube device for selectin-mediated capture of viable circulating tumor cells from blood. *Clin. Chem.* 58(5): 846-53 (2012).
Hughes et al., Rapid isolation of viable circulating tumor cells from patient blood samples. *J. Visual. Exp.* 64: 1-5 (2012).
Jacobs et al., CD44 and HCELL: Preventing hematogenous matastasis at Step 1. *FEBS Lett.* 585(20): 3148-58 (2011).
Shi Yuankai, Progress in Medical Oncology in China Education of Oncologists in China. Peking Union Medical College Press, p. 562 (2013).
Wang Meng et al., Chinese Journal of Gerontology, 34(3), p. 623-625 (2014).
Yang Zhuo et al., Medical Journal of Peking Union Medical College Hospital, 4(2), pp. 191-194 (2013).
Hong et al., The binding avidity of a nanoparticle-based multivalent targeted drug delivery platform. *J. Chem Biol.*, 14(1):107-15 (2007).
Hong et al., Covalent immobilization of p-selectin enhances cell rolling. *Langmuir*, 23(24):12261-8 (2007).
International Preliminary Report on Patentability for International Application No. PCT/US2010/032266, dated Oct. 25, 2011.
International Preliminary Report on Patentability for International Application No. PCT/US2015/019466, dated Sep. 13, 2016.
International Search Report and Written Opinion for International Application No. PCT/US2010/032266, dated Jan. 3, 2011.
International Search Report and Written Opinion for International Application No. PCT/US2015/019466, dated Jun. 1, 2015.
Leckband et al., An approach for the stable immobilization of proteins. *Biotechnol. Bioeng.*, 37(3):227-37 (1991).
Lee et al., Epithelial-mesenchymal transition enhances nanoscale actin filament dynamics of ovarian cancer cells, *J. Phys. Chem. B.*, 117(31):9233-40 (2013).
Ma et al., Transgenic cyclin E triggers dysplasia and multiple pulmonary adenocarcinomas. *Proc. Natl. Acad. Sci.*, 104(10):4089-96 (2013).
Myung et al., Direct measurements on CD24-mediated rolling of human breast cancer MCF-7 cells on E-selectin. *Analytical Chem.*, 83(3):1078-83 (2011).
Myung et al., Dendrimer-mediated multivalent binding for the enhanced capture of tumor cells. *Agnew. Chem. Int. Ed. Eng.*, 50(49):11769-72 (2011).
Myung et al., Differential detection of tumor cells using a combination of cell rolling, multivalent binding, and multiple antibodies. *Analytical Chem.*, 86(12):6088-94 (2014).
Myung et al., Enhanced tumor cell isolation by a biomimetic combination of E-selectin and anti-EpCAM: implications for the effective separation of circulating tumor cells (CTCs). *Langmuir*, 26(11):8589-96 (2010).
Rusmini et al., Protein immobilization strategies for protein biochips. *Biomacromolecules*, 8(6):1775-89 (2007).
Stroock et al., Chaotic mixer for microchannels. *Science*, 295(5555):647-51 (2002).
Myung et al., Multivalent Binding and Biomimetic Cell Rolling Improves the Sensitivity and Specificity of Circulating Tumor Cell Capture, *Clin. Can. Res.*, 24(11):2539-47 (2018).
Trumpp et al., Mechanisms of Disease: cancer stem cells—targeting the evil twin, *Nat. Clin. Pract. Oncol.*, 5:337-47 (2008).

* cited by examiner

Antibody 1  Antibody 2  Antibody 3

BIOMIMETIC MICROFLUID DEVICE FOR CAPTURING CIRCULATING TUMOR CELLS

CROSS REFERENCE TO RELATED APPLICATION

This application claims priority to U.S. Provisional Patent Application No. 61/949,472 filed Mar. 7, 2014, the disclosures of which is incorporated herein by reference in its entirety.

STATEMENT OF GOVERNMENT SUPPORT

This invention was made with government support under CBET-0931472 awarded by the National Science Foundation (NSF). The government has certain rights in the invention.

BACKGROUND

Field of the Invention

The invention relates to a method of capturing Circulating Tumor Cells (CTC) and circulating Cancer Stem Cells (CSC) from a sample, and a multi-channel microfluidic device for performing the method.

Brief Description of Related Technology

Cancer remains one of the world's most devastating diseases, with more than 10 million new cases every year. Although recent advances in diagnostic and therapeutic methods to treat primary tumors have resulted in a decrease in mortality of cancer for the past two years, metastasis of cancer still poses a great challenge as patients often relapse. Disseminated and Circulating tumor cells (DTCs and CTCs, respectively) are known to induce secondary tumor formation at distant sites from primary tumors, known as metastasis. Two major theories describing cancer metastasis, the seed and soil hypothesis and the mechanical trapping theory, are available and the extravasation process for each are similar, consisting of three sequential steps. The metastasis mechanism is known to be initiated by cell rolling—the naturally occurring process utilized to recruit leukocytes to sites of inflammation. In the second step, the cells firmly attach to the endothelial cells. In the third step, the cells transmigrate through the endothelium (diapedesis), resulting in secondary tumor formation.

Research efforts on diagnosis and prognosis of metastatic cancer have concentrated on the detection of DTCs in bone marrow (BM) and CTCs in blood. Detection of DTCs requires aspiration of BM—a process that is invasive, time-consuming, and often painful for the patients, precluding repeated samplings that are necessary for prognosis studies along with therapeutic treatments. Consequently, effective detection of CTCs in peripheral blood of cancer patients holds a promise as an alternative due to its minimal invasiveness and easy samplings (i.e. blood drawing). However, the clinical usage of CTCs has not yet been implemented for routine clinical practice. In fact, the clinical significance of CTCs in patient blood is less clear than that for DTCs in BM. Unlike DTCs in BM that are relatively easy to enrich using Ficoll-based assays or the OncoQuick approach, and other immunomagnetic enrichment procedures, CTCs are extremely rare (estimated to be in the range of one tumor cell in the background of $10^6$-$10^9$ normal blood cells), presenting a tremendous challenge for efficient, clinically significant detection of CTCs.

Tumors are known to comprise tumor initiation cells or circulating cancer stem cells. The circulating cancer stem cells are able to self-renew and generate differentiated progenies to organize a hierarchical cell system in a similar fashion to normal stem cells. These cells exhibit pronounced tumorigenic activity in xenograft transplantation using immunodeficient mice, which indicates the important role of the cells in the development of cancer. Additionally, there is increasing evidence that CSCs could play a crucial role in recurrence after treatment and metastasis (Trumpp & Wiestler, Nat. Clin. Pract. Oncol. 5:337-47, 2008).

Thus, there exists a need for devices and methods to efficiently isolate circulating tumor cells and circulating stem cells with enhanced sensitivity and specificity to aid in diagnosis and prognosis of cancer.

SUMMARY OF THE INVENTION

The biomimetic platform of the invention can accommodate multiple channels on one platform, which can target circulating tumor cells (CTCs) and cancer stem cells (CSCs). The first channel (area 'i' in FIG. 1) can capture CTCs from cancer patient blood, based on specific binding to CTC markers, such as epithelial cell adhesion molecule (EpCAM), human epidermal growth factor receptor-2 (HER-2), Epidermal growth factor receptor (EGFR), Carcinoembryonic antigen (CEA), Prostate specific antigen (PSA), CD24, and folate binding receptor (FAR). The captured CTCs can be detached from area 'i' using trypsin or other EDTA-based detaching solution. Among captured CTCs, more stem-like CTCs, potentially CSCs, then can be differentiated using the other channel (area 'ii" in FIG. 1) specific to CSC. For cell differentiation, stem cell markers such as CD44, CXCR1, N-Cadherin, and CD133 can be utilized on the second channel. This concept of capturing and differentiating of CTC and CSC in situ could be extended to multiple channel systems. One of examples for multiple channel system, three channel device, is shown in FIG. 1B. In addition, this three channel flow chamber could be used for other purposes: e.g. simultaneous CTC capturing from three blood specimens of different cancer patients for high-throughput screening and capture of CTCs and CSCs. Exemplary dimensions for both two and three channel flow chambers are indicated in FIG. 2. To maximize the CTC detection efficiency, parameters for surface functionalization, i.e. the width of E-selectin and antibodies, and the angle of antibody stripes, could be changed as depicted in FIG. 3.

The device of the invention improves sensitivity and specificity for the isolation of CTCs and CSCs. First, immobilization of a cell rolling-inducing agent, such as E-selectin, improves the isolation of CTCs and CSCs from red blood cells and plasma. Importantly, the naturally occurring cell rolling phenomenon is one of the most efficient ways to recruit the fast-flowing cells to the capture surface, eliminating the need for flow fluctuation that often results in the clogging and non-specific capturing issues. Second, immobilization of tumor cell-specific and/or stem-cell specific capturing agents, such as antibodies, through dendrimer nanolinkers achieves strong multivalent binding to enhance capture efficiency. Third, the modular nature of device of the invention allows for use of any marker as capturing agents, which is ideally suited for effective detection of CTCs and CSCs with highly heterogeneous phenotypes. In addition, the optimized multi-channel device of the invention achieves highly efficient capture of CTCs as well as CSCs, at a high throughput. For example, at the same flow rate of 0.4 dyn/cm$^2$, or 50 µL/min with a single channel design, the three-channel design will achieve the analysis of 1 mL of blood in 7 min, instead of 20 min.

The invention provides for methods of capturing CTC and CSC from a sample comprising the step of introducing said sample into a flow based device wherein the device comprises at least two chambers, the first chamber comprises an immobilized cell rolling-inducing agent and an immobilized CTC specific capturing agent and the second chamber comprising an immobilized cell rolling-inducing agent and an immobilized CSC specific capturing agent, and said sample introduced into the device under conditions that allow a CTC and a CSC to bind to the cell rolling-inducing agent and the capturing agent.

The sample is any fluid that comprises CTCs and/or CSCs such as blood, lymphatic fluid or cerebrospinal fluid.

In the methods of the invention, the capturing agent, for capturing CTC and/or CSC, is any agent that specifically binds to a CTC or a CSC such as an antibody, an antibody fragment, an engineered antibody, folic acid, transferrin, a peptide, and an aptamer.

In any of the methods of the invention, the CTC specific capturing agent specifically binds a moiety on a CTC surface, such as an antibody, an antibody fragment, an engineered antibody, folic acid, transferrin, a peptide, and an aptamer. For example, the capturing agent binds to epithelial cell adhesion molecule (EpCAM), human epidermal growth factor receptor-2 (HER-2), epidermal growth factor receptor (EGFR), carcinoembryonic antigen (CEA), Prostate specific antigen (PSA), CD24, or folate binding receptor (FAR) to name a few. In addition, the CTC specific capturing agent is a peptide such as an RGD peptide.

In any of the methods of the invention, the CSC specific capturing specifically binds a moiety on a CSC surface, such as an antibody, an antibody fragment, an engineered antibody, folic acid, transferrin, a peptide, or an aptamer. For example, the CSC specific capturing agent binds to CD44, CXCR1, N-Cadherin, CD10, CD127 or CD133, to name a few.

In any of the methods of the invention, the capturing agent, for capturing CTC and/or CSC, is immobilized via attachment to a surface of the device or the agent is immobilized via attachment to a linker, said linker attached to a surface of the device.

The linker attaching a capturing agent to the surface of the device used in the methods of the invention is a polymeric nanolinker such as a modified poly(amidoamine) dendrimer covalently attached to polyethylene glycol. In one aspect, the modified poly(amidoamine) dendrimer is selected from the group consisting of a generation 3, a generation 4, a generation 5, a generation 6, a generation 7, a generation 8, and a generation 9 modified poly(amidoamine) dendrimer. In another aspect, the polymeric nanolinker comprises poly-ester-n-carboxylate-1-alkyne dendron covalently attached to polyethylene glycol, wherein n is 8, 16, 32, 64, or 128.

The invention provides for any of the methods of the invention which further comprise the step of applying a shear stress between 0.05 and 10 dyn/cm$^2$ on the sample introduced into the device. In another aspect of the method, the shear stress is between 0.1 dyn/cm$^2$ and 2 dyn/cm$^2$. In yet another aspect of the method, the shear stress is about 0.16 dyn/cm$^2$.

In any of the methods of the invention, the cell rolling-inducing agent is a selectin or a CTC or CSC binding fragment of a selectin. For example, the selectin is selected from the group consisting of E-selectin, P-selectin, and L-selectin.

In another aspect of the method, the immobilized cell rolling-inducing agent and the immobilized capturing agent are arranged in a substantially uniform manner.

In yet another aspect of the method, the immobilized cell rolling-inducing agent and the immobilized capturing agent are arranged in a pattern.

In any of the methods of the invention, the cell rolling-inducing agent is covalently attached to a surface of the device. For example, the cell-rolling inducing agent is covalently attached to the surface via a chemical moiety selected from the group consisting of an epoxy group, a carboxyl group, a thiol group, an alkyne group, an azide group, a maleimide group, a hydroxyl group, an amine group, an aldehyde group, and a combination thereof.

In yet another aspect of any of the methods of the invention, the cell rolling-inducing agent is immobilized to a surface of the device via a linker. For example, the linker is selected from the group consisting of a dendrimer, a dendron, a dextran, polyethylene glycol, poly(L-lysine), poly(L-glutamic acid), polyvinyl alcohol, polyethylenimine, poly(lactic acid), poly(glycolic acid), and a combination thereof.

Also provided herein is a flow based multichannel device for capturing a Circulating Tumor Cell (CTC) and a circulating Cancer Stem Cell (CSC) from a sample, comprising: (a) a first channel comprising a cell capture surface and a flow mobilization surface, wherein a CTC specific capturing agent and a cell rolling-inducing agent are immobilized to the cell capture surface, and (b) a second channel comprising a cell capture surface and a flow modification surface, wherein a CSC capturing agent and a cell rolling-inducing agent are immobilized to the cell capture surface. The term "multichannel" refers to two or more channels. The devices of the invention may have 2 channels, 3 channels, 4 channels, 5 channels, 6 channels, 7 channels, 8 channels, 9 channels or 10 or more channels.

In one aspect of the device, the multiple channels within the device are connected and the sample will flow between the channels. In another aspect, the device has multiple inputs and multiple outputs, e.g. each channel has its own input and output and the channels are not connected, or each channel has its own input and the channels are connected with a single or multiple outputs.

In any of the devices of the invention, the cell rolling-inducing agent is a selectin or a CTC or CSC binding fragment of a selectin. In another aspect of the device, the selectin is E-selectin, P-selectin, or L-selectin.

In any of the devices of the invention, the CTC specific capturing agent specifically binds a moiety on a CTC surface, such as an antibody, an antibody fragment, an engineered antibody, folic acid, transferrin, a peptide, or an aptamer. For example, the capturing agent binds to epithelial cell adhesion molecule (EpCAM), human epidermal growth factor receptor-2 (HER-2), epidermal growth factor receptor (EGFR), carcinoembryonic antigen (CEA), Prostate specific antigen (PSA), CD24, or folate binding receptor (FAR). In addition, the CTC specific capturing agent is a peptide such as an RGD peptide.

In any of the devices of the invention, the CSC capturing agent specifically binds a moiety on a CSC surface, such as an antibody, an antibody fragment, an engineered antibody, folic acid, transferrin, a peptide, and an aptamer. For example, the capturing agent binds to CD44, CXCR1, N-Cadherin, CD10, CD127 or CD133.

In any of the devices of the invention, the capturing agent, for capturing CTC and/or CSC, is immobilized via attachment to a surface of the device or the agent is immobilized via attachment to a linker, said linker attached to a surface of the device.

The linker attaching a capturing agent to the surface of any of the devices of the invention is a polymeric nanolinker such as a modified poly(amidoamine) dendrimer covalently attached to polyethylene glycol. In one aspect, the modified poly(amidoamine) dendrimer is selected from the group consisting of a generation 3, a generation 4, a generation 5, a generation 6, a generation 7, a generation 8, or a generation 9 modified poly(amidoamine) dendrimer. In another aspect, the polymeric nanolinker comprises polyester-n-carboxylate-1-alkyne dendron covalently attached to polyethylene glycol, wherein n is 8, 16, 32, 64, or 128.

In another aspect of any of the devices of the invention, the cell rolling-inducing agent and the capturing agent are arranged in a substantially uniform manner.

In another aspect of any of the devices of the invention, the cell capture surface comprises a pattern of first and second regions, the first region comprising the cell rolling-inducing agent, and the second region comprising the capture agent. In one aspect, the first region further comprises the capture agent.

In another aspect of any of the devices of the invention, the first and second regions are arranged in an alternating pattern.

In any of the devices of the invention, the cell rolling-inducing agent is covalently attached to the cell capture surface. For example, the covalent attachment is through a chemical moiety such as an epoxy group, a carboxyl group, a thiol group, an alkyne group, an azide group, a maleimide group, a hydroxyl group, an amine group, an aldehyde group, or combinations thereof.

In any of the devices of the invention, the cell rolling-inducing agent is immobilized to a surface of the microfluidic device via a linker. For example, the linker is a dextran, a dendrimer, polyethylene glycol, poly(L-lysine), poly(L-glutamic acid), polyvinyl alcohol, polyethylenimine, poly (lactic acid), poly(glycolic acid), and a combination thereof.

Other features and advantages of the present disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

DETAILED DESCRIPTION OF THE INVENTION

Figure 1:
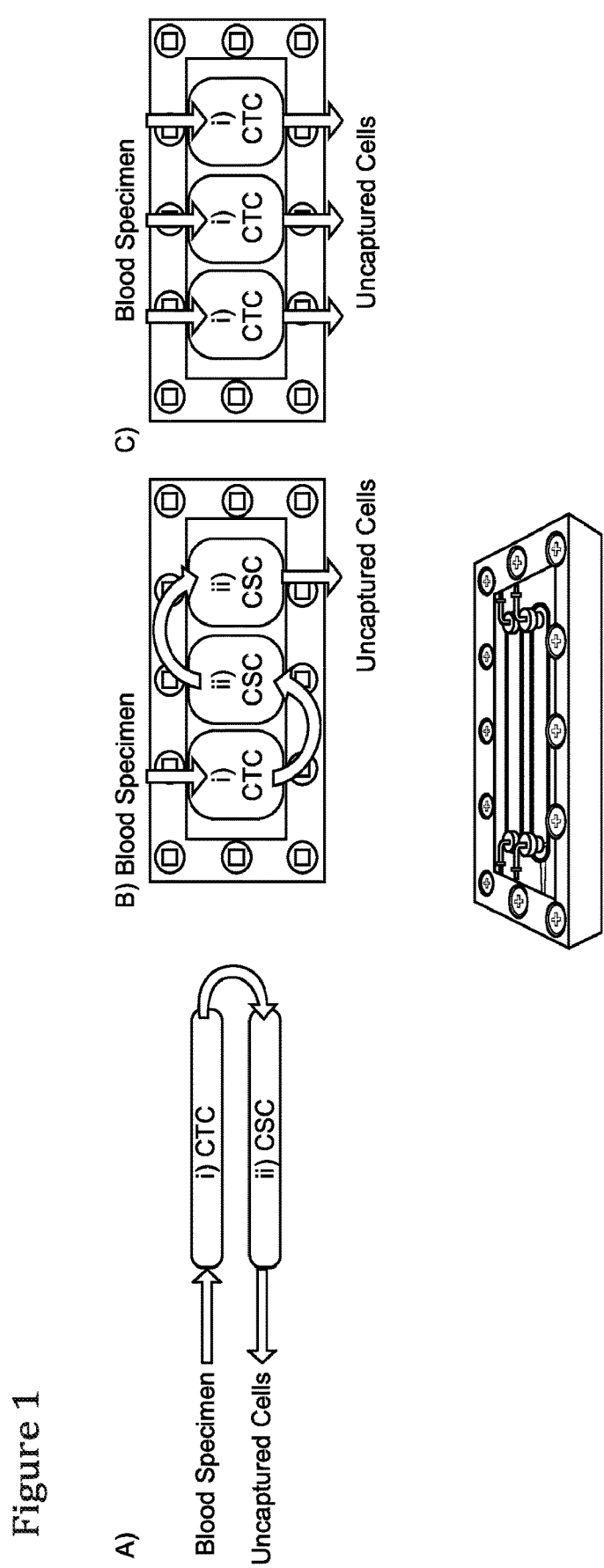
FIG. 1 provides the biomimetic platform model for CTC and CSC capture and differentiation. In Panel A: among CTCs captured on the area 'i' from cancer patient blood, stem-like cancer cells can be continuously differentiated and isolated using the area 'ii'. This concept of capturing and differentiating of CTC and CSC in situ could be further applied as a three channel device as shown in Panel B. The three channel device could be used for high-throughput screening of multiple blood specimens as shown in Panel C.
Figure 2A:
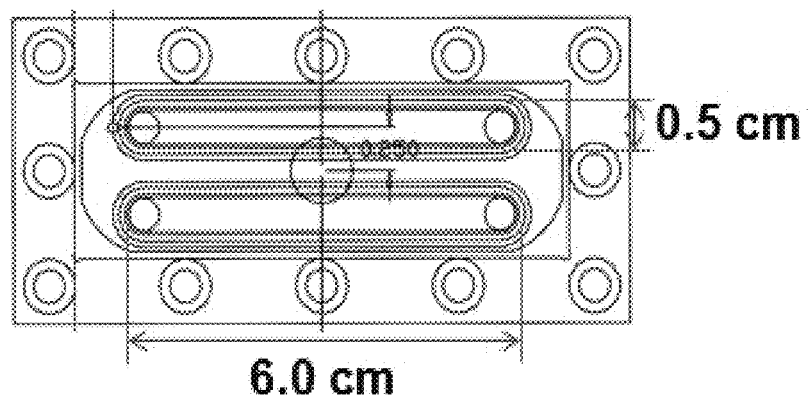
FIG. 2 provides prototypes of flow chambers for multichannel flow based device of the invention. For example, the two or three channel flow chambers can be fabricated as the indicated dimensions.
Figure 2B:
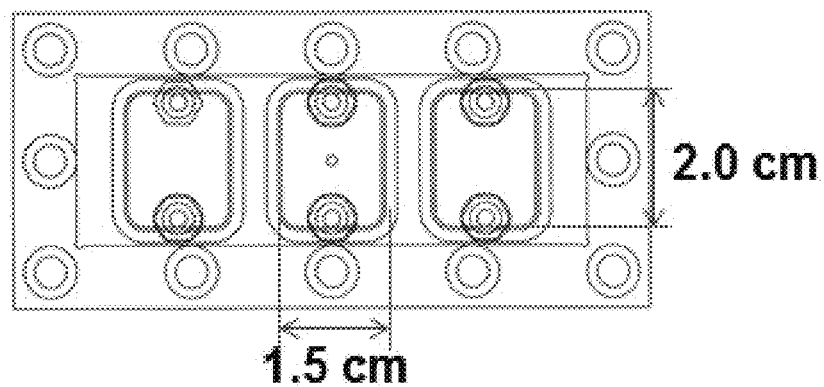
Figure 3:
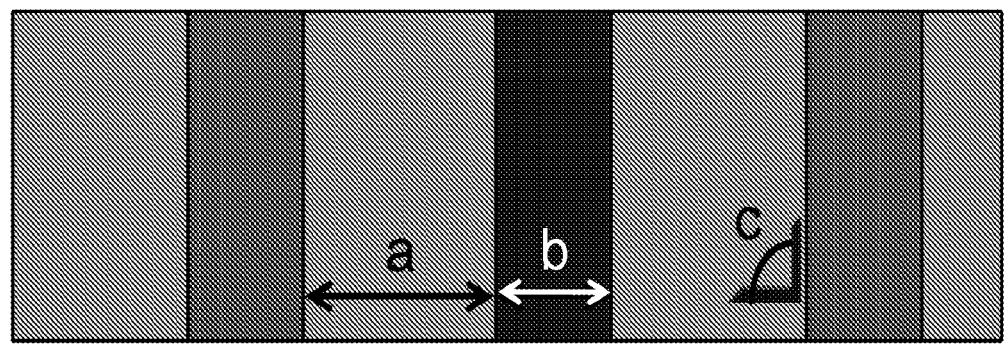
FIG. 3 provides a schematic of multichannel flow based device of the invention. To obtain the highest CTC detection sensitivity and specificity, the parameters for surface functionalization, such as the width of E-selectin patterns (a), the width of antibody patterns (b), and angle of antibody patterns, could be modified.

It must be noted that as used herein and in the appended claims, the singular forms "a," "and," and "the" include plural referents unless the context clearly dictates otherwise.

In one aspect, a device for capturing CTCs and CSCs from a sample includes at least two channels, wherein each channel comprises a cell capture surface and a flow modification surface. For example, in one channel the cell capture surface includes a cell rolling-inducing agent and a CTC specific capturing agent and in another channel, the cell capture surface includes a cell rolling-inducing agent and a CSC specific capturing agent. A method for capturing CTCs and CSCs from a sample, in one aspect, includes introducing the sample into the device under conditions that allow a CTC and a CSC bind to the cell-rolling-inducing agent and a capturing agent Optionally, the flow modification surface includes one or more structures arranged to induce a rotational flow in a sample flowing through the channel. The flow modification surface induces a rotational flow in the sample, which may allow for enhanced contact of the cells with the cell capture surface, and, thus, for more efficient CTC and CSC capture.

The methods of the invention provide for high throughput separation of biological samples in a physiological range of flow rates from about 200 to 500 μL/min. In some embodiments, a shear stress of between 0.05 dyn/cm$^2$ and 10 dyn/cm$^2$ is applied to the sample introduced into the microfluidic device 10. In some embodiments, a shear stress of between 0.1 dyn/cm$^2$ and 2 dyn/cm$^2$ is applied to the sample introduced into the microfluidic device 10. In some embodiments, the shear stress is about 0.05, about 0.10, about 0.15, about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, about 1.0, about 1.1, about 1.2, about 1.3, about 1.4, about, 1.5, about 1.6, about 1.7, about 1.8, about 1.9, about 2.0, about 2.1, about 2.2, about 2.3, about 2.4, about, 2.5, about 2.6, about 2.7, about 2.8, about 2.9, about 3.0, about 3.1, about 3.2, about 3.3, about 3.4, about, 3.5, about 3.6, about 3.7, about 3.8, about 3.9, about 4.0, about 4.1, about 4.2, about 4.3, about 4.4, about, 4.5, about 4.6, about 4.7, about 4.8, about 4.9, about 5.0, about 5.1, about 5.2, about 5.3, about 5.4, about, 5.5, about 5.6, about 5.7, about 5.8, about 5.9, about 6.0, about 6.1, about 6.2, about 6.3, about 6.4, about, 6.5, about 6.6, about 6.7, about 6.8, about 6.9, about 7.0, about 7.1, about 7.2, about 7.3, about 7.4, about, 7.5, about 7.6, about 7.7, about 7.8, about 7.9, about 8.0, about 8.1, about 8.2, about 8.3, about 8.4, about, 8.5, about 8.6, about 8.7, about 8.8, about 8.9, about 9.0, about 9.1, about 9.2, about 9.3, about 9.4, about, 9.5, about 9.6, about 9.7, about 9.8, about 9.9, about 10.0 dyn/cm$^2$. In some embodiments, the shear stress is about 0.16 dyn/cm$^2$.

I. Microfluidic Device

The device of the invention includes at least two channels having a cell capture surface and a flow modification surface. The cell capture surface can be disposed opposite the flow modification surface. For example, the cell capture surface can be disposed on the bottom surface of the channel and the flow modification surface can be disposed on the top surface of the channel, opposite the cell capture surface. Alternatively, the flow modification can be disposed adjacent to the cell capture surface. In yet another embodiment, the cell capture surface and the flow modification surface can be incorporated into a single surface. The channel can be, for example, a closed channel having four walls. The cell capture surface and/or the flow modification surface can be disposed on multiple walls of the channel.

The multiple channels within the device can be connected and the sample will flow between the channels. In another aspect, the device can have multiple inputs and multiple outputs, e.g. each channel has its own input and output and the channels are not connected, or each channel has its own input and the channels are connected with a single or multiple outputs. The multiple channels can be of uniform shape and/or size. Alternatively, the multiple channels can have different shapes and sizes within a single device.

The channels can have any suitable cross-sectional shape. For example, the channels can be rectangular, triangular, circular, or elliptical. The dimension of the microfluidic device can be optimized to maximum fluid rotation while minimizing fluid resistance using the following equation:

$$R = \frac{12\mu L}{wh^3}$$

where μ is the kinematic viscosity, L is the channel length, w is the channel width, and h is the channel height.

For example, the channel can have a height of about 50 μm to about 600 μm, about 100 μm to about 500 μm, about 200 μm to about 400 μm. Other suitable heights include, for example, about 50, 100, 150, 200, 250, 300, 350, 400, 450, 500, 550, or 600 μm. The channels can have a width of about 200 μm to about 2000 μm, about 400 μm to about 1500 μm, about 500 μm to about 1000 μm, or about 600 μm to about 800 μm. Other suitable widths include, for example, about 200, 300, 400, 500, 600, 700, 800, 900, 1000, 1100, 1200, 1500, 1600, 1700, 1800, 1900, or 2000 μm. The channels can have a length of about 200 μm to about 5000 μm, about 400 μm to about 4000 μm, about 600 μm to about 2000 μm, or about 800 μm to about 1000 μm. Other suitable lengths include, for example, about 200, 300, 400, 500, 600, 700, 800, 900, 1000, 1500, 2000, 2500, 3000, 3500, 4000, 4500, or 5000 μm.

The cell capture surface includes a cell rolling-inducing agent and a CTC and/or CSC specific capturing agent attached to a substrate. The substrate can be, for example, glass, plastics (or polymer-coated), hydrogels, matrigel, or extracellular matrix (ECM)-coated substrates. The cell rolling-inducing agent and the capturing agent can be immobilized on the substrate either directly or indirectly, using, for example a linker. The cell rolling-inducing agent and the capturing agent can be arranged uniformly across the cell capture surface. For example, the cell capture surface can include alternating regions having the cell rolling-inducing agent and the capture agent. The alternating regions can have substantially the same widths or the widths can vary among the regions. The regions including the cell rolling-inducing agent and the capturing agent can be arranged, for example, as parallel to or at angles relative to the direction of the flow through the channel. For example, the regions can be arranged tangentially to the direction of the flow through the channel.

Flow modification surfaces are well known in the art. Any known flow modification surface can be used. For example, the flow modification surface can optionally include one or more ridges, extending from the surface into the channel. The ridges are shaped, sized, and oriented so as to induce a rotational flow in a sample flowing through the channel. The cell capture surface and the flow modification surface can be included on a single surface of the device, for example, by coating the flow modification surface with the cell rolling-inducing agent and the capture agent. For example, the ridges can be coated with the cell rolling-inducing agent and the capture agent. All or portions of the ridges can be coated. For example, the sidewalls of the ridges can be coated with the cell rolling-inducing agent and the capture agent. The induction of rotational flow in the sample can enhance cell capture efficiency. Cells having low diffusivity will have a tendency to remain the region of the channel at which they enter. For example, hematologic cells have an inherently low diffusivity due to their large diameter. This detrimentally affects the cell capture process when the cells enter the channel distant from the cell capture surface. For example, if a blood cell enters the microfluidic channel near the top, it will likely remain near the top as it travels several centimeters along a microchannel, limiting interaction of the cells with biofunctionalized substrates located at the bottom of the channel. The induction of a rotational flow in the sample will force the cells towards the cell capture surface, thereby enhancing the contact between the cells and the cell capture surface.

The ridges can have any suitable cross sectional shape, such as, for example, rectangular, circular, elliptical, or triangular. The ridges can have a thickness of about 10 µm to about 300 µm, about 50 µm to about 300 µm, about 100 µm to about 250 µm, or about 150 µm to about 200 µm. Other suitable thicknesses t include about 10, 15, 20, 25, 30, 35, 40, 45, 50, 55, 60, 65, 70, 75, 80, 85, 90, 95, 100, 125, 150, 175, 200, 225, 250, 275, or 300 µm. The ridges can have a width of about 50 µm to about 300 µm, about 100 µm to about 250 µm, or about 150 µm to about 200 µm. Other suitable widths include about 50, 75, 100, 125, 150, 175, 200, 225, 250, 275, or 300 µm. The distance between adjacent ridges can be about 50 µm to about 500 µm, about 100 µm to about 400 µm, or about 200 µm to about 300 µm. Other suitable distances include about 50, 100, 150, 200, 250, 300, 350, 400, 450, or 500 µm. The distance between adjacent ridges can be substantially uniform across the flow modification surface or can vary.

The ridges can be substantially linear, extending, for example, in a direction perpendicular to the flow. The ridges can have a herringbone structure. The ridges can be angled relative to the direction of flow. For example, the ridges can be angled perpendicularly or obliquely relative to the direction of flow. In one embodiment, the ridges are at a 45° angle relative to the direction of flow F. Other suitable angles include about 45°, 50°, 55°, 60°, 65°, 70°, 75°, 80°, 85°, 90°, 100°, 110°, 120°, 130°, 140°, 150°, 160° and 170°. The one or more ridges can be angled uniformly. Alternatively, the angle of the ridges can vary across the channel to induce different rotational properties to a sample flowing through the channel.

The one or more ridges can be arranged in a pattern. For example, the flow modification surface can include first regions having the one or more ridges and second regions that are devoid of ridges. Alternatively, the second regions can include ridges that are oriented, sized, and/or shaped differently than the ridges of the first regions. The flow modification surface can further include third regions that are completely devoid of ridges. Any suitable number of regions having differently sized, oriented, and/or shaped ridges can be included on the flow modification surface. The first and second regions can alternate, for example, uniformly across the flow modification surface.

The microfluidic device can be fabricated by preparing the cell capture surface with regions having the cell rolling-inducing agent and regions having the capturing agent. A microfluidic channel having a flow modification surface can then be attached to the cell capture surface.

The cell capture surface can be formed by patterning the cell rolling-inducing agent and the capturing agent on a substrate, for example, a glass slide. Any known method of forming regions of a cell rolling-inducing agent and a capturing agent can be used to form the cell capture surface. The cell rolling-inducing agent and the capturing agent can be patterned, for example, using a polymer stencil, for example, a PDMS stencil. The stencil can be formed as is known in the art, for example, using photolithography. A photoresist can be coated on a wafer and selectively exposed using a photomask. The photoresist is then developed, resulting in unexposed portions of the photoresist being removed, thereby forming a negative mold for the stencil. A polymer, such as PDMS, can then be poured onto the negative mold and cured, thereby resulting in the stencil. The stencil includes one or more structures protruding from a first surface. The size, orientation, and shape of the protruding structures are substantially the same as the size, orientation, and shape of the desired regions of the cell rolling-inducing agent and the capturing agent. When placed on a substrate, the protruding structures function to mask portions of the substrate. The cell rolling-inducing agent or the capturing agent can be attached to the unmasked portions of the substrate. The stencil can then be removed and the exposed portions of the substrate can be filled with the cell rolling-inducing agent or the capturing agent, thereby forming the cell capture surface.

The cell rolling-inducing agent and the capturing agent can be attached to the substrate using, for example, physisorption or plasma ablation. For example, the agents can be attached using microfluidic adsorption in which the desired agent is placed in a soluble media and injected through a microfluidic channel placed onto the substrate. The solution is allowed to adsorb to the surface over several hours. This technique is advantageous when the desired agents are sensitive to or damaged by heat.

Methods are well known in the art for preparing surfaces with different densities and patterns of suitable groups for covalent bonding (e.g., see Rusmini et al., *Biomacromolecules* 8: 1775-89 (June 2007) and Leckband et al., *Biotechnology and Bioengineering* 37: 227-237 (1991), the entire contents of both of which are incorporated herein by reference). In some embodiments, the density of a capturing agent and/or a cell rolling-inducing agent ranges from about 10 $ng/cm^2$ to about 600 $ng/cm^2$. In some embodiments, the density of a capturing agent and/or a cell rolling-inducing agent is greater than about 30 $ng/cm^2$. For example, in some embodiments, the density of a capturing agent and/or a cell rolling-inducing agent ranges from about 30 $ng/cm^2$ to about 360 $ng/cm^2$. In some embodiments, the density of a capturing agent and/or a cell rolling-inducing agent ranges from about 50 $ng/cm^2$ to about 300 $ng/cm^2$. In some embodiments, the density of a capturing agent and/or a cell rolling-inducing agent ranges from about 100 $ng/cm^2$ to about 200 $ng/cm^2$.

The channel and the flow modification surface can be formed as is known in the art. See Stroock et al., Science 295: 647-51, the disclosure of which is incorporated herein by reference in its entirety. The flow modification surface can be formed using soft-lithography. For example, the flow modification surface can be formed using a photoresist, such as a dual height SU-8 photoresist mold. The mold is prepared by first spinning and patterning the microfluidic channel. Before developing the channel pattern, a second photoresist layer is spun onto the mold to generate a pattern for the ridges of the flow modification surface. Alignment markers may be added to facilitate proper orientation of the second photoresist layer. The mold is then exposed, hard baked, and developed, thereby resulting in a mold that contains a channel with structures that will cast the ridges of the flow modification surface. The resulting mold is then coated with a polymer, for example, PDMS, to form the channel and the flow modification surface.

II. Cell Rolling

The chamber of microfluidic device of the invention comprises an immobilized cell rolling-inducing agent. The formation of transient ligand-receptor interactions occurs commonly between cells flowing in the blood and the vascular endothelium; this physiological process is known as cell rolling. Cell rolling is known to play a key role in biologically important processes such as recruitment of leukocytes to sites of inflammation, homing of hematopoietic progenitor cells after intravenous injection, and CTC-induced metastasis. This behavior is typically mediated by dynamic interactions between selectins (e.g., E-, P-, L-selectins) on the vascular endothelial cell surface and membrane proteins including P-selectin glycoprotein ligand-1 (PSGL-1). A person of skill in the art will recognize that any molecule capable of inducing CTCs tor CSCs to undergo cell rolling can be used to practice the disclosed methods and prepare the disclosed devices.

In some embodiments of the disclosure, the cell rolling-inducing agent is a selectin. In another embodiment, the selectin is endothelial (E)-selectin. In yet another embodiment, the selectin is P-selectin. In another embodiment, the selectin is L-selectin. Moreover, fragments of selectins which retain the ability to bind CTCs are specifically envisioned to be within the scope of the disclosure.

E-selectin (CD62E) is particularly noteworthy in disease by virtue of its expression on activated endothelium and on bone-skin microvascular linings and for its role in cell rolling, cell signaling, and chemotaxis. Many studies point to the key role played by E-selectin in being involved in the adhesion and homing of various types of cancer cells such as prostate, breast, and colon carcinoma cells. E-selectin is synthesized de novo by endothelial cells in response to inflammatory cytokines, such as interleukin-1β (IL-1β) and tumor necrosis factor-α (TNF-α). Thus, cell separation based on the cell rolling behavior is being exploited as it mimics physiological processes and eliminates labeling and label removal steps that are necessary for other immune-labeling detection methods. However, given that a large class of cells, including leukocytes, platelets, neutrophils, mesenchymal and hematopoietic stem cells, and metastatic cancer cells, exhibits rolling on selectins, rolling-based detection for specific cell types from cell mixtures or whole blood has limitations to achieve sufficient specificity, which has hindered translation of the technology to a clinically significant device. The methods and devices of the disclosure overcome this limitation by coupling the cell rolling-inducing agent with an immobilized capturing agent. Without intending to be bound by any particular theory, it is believed that the cell rolling-inducing agent causes a circulating tumor cell (CTC) to exhibit the "rolling" behavior (described above) on a surface of the microfluidic device. The rolling CTC then contacts the immobilized capturing agent, and is thereby captured (i.e. immobilized) by the device.

Any covalent chemistry may be used to immobilize cell rolling-inducing agents to a surface of the microfluidic device. In some embodiments, cell rolling-inducing agents are attached to a surface through one or more chemical moieties. In general, the bond between the chemical moiety and the surface is covalent. Without limitation, in some embodiments, the chemical moiety comprises an epoxy group, a carboxyl group, a thiol group, an alkyne group, an azide group, a maleimide group, a vinyl group, a hydroxyl group, an amine group, an aldehyde group, and combinations thereof.

In some embodiments, the cell-rolling inducing agent is immobilized to a surface of the microfluidic device via a linker. In some embodiments, the linker is selected from the group consisting of a dendrimer, a dendron, a dextran, polyethylene glycol, poly(L-lysine), poly(L-glutamic acid), polyvinyl alcohol, polyethylenimine, poly(lactic acid), poly(glycolic acid), and combinations thereof.

The rolling effect for capturing CTC used in the devices and methods of the present invention are described in detail in PCT Publication No. WO2010/124227 and US Patent Publication No. 20120077246, which are incorporated by reference herein in their entirety.

III. Cell Capture

A. Capturing Agent

The channels of the microfluidic device of the invention comprise an immobilized capturing agent. A person of skill in the art will appreciate that any molecule capable of selectively binding to circulating tumor cells will be useful as a capturing agent. Specific examples of such molecules exhibiting selective binding to circulating tumor cells include antibodies (or antibody fragments), folic acid, transferrin, certain peptides, and aptamers. Examples of antibodies include, but are not limited to, Trastuzumab (Herceptin), Bevacizumab (Avastin), anti-CD33 antibody (Mylotarg), anti-CD20 antibodies (Zevalin and Bexxar), and their fragments and engineered forms (e.g. diabody, avimer, etc.). Examples of peptides include, but are not limited to, RGD and NGR Epithelial cell adhesion molecule (EpCAM) is frequently overexpressed by a variety of carcinomas such as lung, colorectal, breast, prostate, head and neck, and hepatic origin, but is absent from hematologic cells. Thus, to allow specific binding (i.e. "capturing") of CTCs while avoiding binding of non-CTC cells, in some embodiments, the capturing agent is an anti-EpCAM antibody. Anti-EpCAM antibody is commercially available from several sources including, for example, R&D Systems, Abcam, and Millipore. Alternatively, anti-EpCAM antibodies useful for practicing the methods of the disclosure or generating the devices of the disclosure can be generated by any method known in the art.

As used herein, the terms "antibody" and "immunoglobulin" are understood to mean (i) an intact antibody (for example, a monoclonal antibody or polyclonal antibody), (ii) antigen binding portions thereof, including, for example, an Fab fragment, an Fab' fragment, an (Fab')$_2$ fragment, an Fv fragment, a single chain antibody binding site, an sFv, (iii) bi-specific antibodies and antigen binding portions thereof, and (iv) multi-specific antibodies and antigen binding portions thereof.

As used herein, the terms "bind specifically," "specifically bind" and "specific binding" are understood to mean that the antibody has a selective binding affinity for a particular antigen of at least about $10^6$ M$^{-1}$, more preferably, at least about $10^7$ M$^{-1}$, more preferably at least about $10^8$ M$^{-1}$, and most preferably at least about $10^{10}$ M$^{-1}$. Appropriate controls can be used to distinguish between "specific" and "non-specific" binding.

As used herein, the term "CTC specific capturing agent" is understood to mean an agent that specifically binds to a CTC, e.g. the agent specifically binds to a moiety on the surface of the CTC. In addition, the term "CSC specific capturing agent is understood to mean an agent that specifically binds to a CSC, e.g. the agent specifically binds to a moiety on the surface of the CSC.

In some embodiments, the capturing agent is transferrin. Transferrin is an iron binding transport protein, which can bind two atoms of ferric iron in association with the binding of an anion, for example, bicarbonate. Transferrin is responsible for the transport of iron from sites of absorption and heme degradation to those of storage and utilization. The transferrin receptor (TfR) is known to be overexpressed in a broad range of cancers, making transferrin useful as a capturing agent.

In some embodiments, the capturing agent is an RGD peptide, a cRGD peptide, RGD mimetics, peptides or proteins containing the RGD sequence, structural or functional equivalents thereof, or combinations thereof. The RGD or RGD mimetics described herein include any peptides or peptide mimetics resulting from the modification of the cyclic Arg-Gly-Asp peptide. The modification can be on the pendant groups and/or on the backbone of the peptide. Peptide synthesis, including the synthesis of peptide mimetics, is well documented and can be readily achieved via, for example, combinatorial chemistry.

In some embodiments, the capturing agent is folic acid. Folic acid is known to bind to a tumor-associated antigen known as the folate receptor (FR), making folic acid useful as a capturing agent.

B. Multivalent Effect

Multivalent interactions—the simultaneous binding event of multiple ligands to multiple receptors in biological systems—have been extensively investigated to promote targeting of specific cell types. These activities are also central to a number of pathological processes, including the attachment of viral, parasitic, mycoplasmal, and bacterial pathogens. Studies with biological multivalent inhibitors have yielded quantitative measurements of binding avidities, with increases on the order of 1 to 9 orders of magnitude.

In some aspects of the disclosure, the multivalent effect is accomplished by immobilizing the capturing agent on the substrate of the cell capture surface via attachment to a linker, which is directly attached to the substrate of the cell capture surface. In some embodiments, the linker is a polymeric nanolinker. In some embodiments, the polymeric nanolinker is a modified poly(amidoamine) (PAMAM) dendrimer.

The nanolinker may be a dendritic polymer. Any of the known dendritic architectures may be used, including, for example, dendrimers, tecto-dendrimers, regular dendrons, dendrigrafts, and hyperbranched polymers. Dendritic star-branched polymers having a plurality of arms emanating from a nucleus may also be used. Accordingly, as used herein, dendritic polymers are polymers with densely branched structures having a large number of terminal reactive groups. A dendritic polymer includes several layers or generations of repeating units, usually referred to as branch cells, which all contain one or more branch points. Dendritic polymers, including dendrimers and hyperbranched polymers, are prepared by reaction of monomeric units having two or more reactive groups, or a combination of monomeric units in which at least one of the monomeric units has at least three reactive groups. The dendrimers which can be used include those comprised of a plurality of dendrons that emanate from a common core which can be a single atom or a group of atoms. Each dendron generally consists of terminal surface groups, interior branch junctures having branching functionalities greater than or equal to two, and divalent connectors that covalently connect neighboring branching junctures.

Methods of preparing and characterizing dendrimers, dendrons, hyperbranched polymers, star-branched polymers, dense star-branched polymers and hypercomb-branched polymers are all well known in the art and thoroughly described in the literature. Dendrons are regular-branched polymeric molecules and their structures can be precisely controlled at the molecular level and they have unique properties. They are wedge-shaped and comprise a focal point from which the branches originate. Different dendrons may have different numbers of branches extending from each branch and different numbers of layers. In some embodiments of the disclosure, the polymeric nanolinker comprises polyester-n-carboxylate-1-alkyne dendron covalently attached to polyethylene glycol, wherein n is 8, 16, 32, 64, or 128.

Specific examples of dendritic polymers that may be used include poly(amidoamine) (PAMAM) dendrimers, dendrigrafts and hyperbranched polymers; poly(benzylether) dendrimers, dendrigrafts and hyperbranched polymers; polyester dendrimers and hyperbranched polymers; poly(propyleneimine) (PPI) dendrimers, dendrigrafts and hyperbranched polymers; organo silicon-containing dendrimers, dendrigrafts and hyperbranched polymers, polystyrene arborescent polymers.

PAMAM dendrimers have been reported to be an excellent mediator for facilitated multivalent effect because the geometry of the dendrimer preorganizes the ligands into a small region of space as compared to what is obtained if one conjugates the ligands to a similar molecular weight linear polymer. Thus, one has "prepaid" the entropy penalty for localizing the ligands. Second, the dendrimer structure allows all ligands to address the cell surface. This is not necessarily the case for a similar molecular weight hyperbranched polymer in which tangled or cross-linked chains may prevent the needed ligand orientation. PAMAM dendrimers are quite flexible and easily deform from the spherical shape adopted in isotropic media to a disc-like structure upon interaction with a surface. This combination of preorganization, polymer backbone topology, and easy deformability, makes the PAMAM dendrimer an effective material for achieving multivalent binding to cell surfaces. Furthermore, the multivalent effect can significantly increase specificity and sensitivity of detection of target proteins or cells. By immobilizing PAMAM dendrimers conjugated with cancer cell specific markers such as anti-EpCAM, specificity and sensitivity of the surface is substantially increased by the multivalent effect.

In some embodiments, the PAMAM dendrimer is covalently attached to polyethylene glycol.

In some embodiments, the PAMAM dendrimer is selected from the group consisting of a generation 3 PAMAM dendrimer, a generation 4 PAMAM dendrimer, a generation 5 PAMAM dendrimer, a generation 6 PAMAM dendrimer, a generation 7 PAMAM dendrimer, a generation 8 PAMAM dendrimer, and a generation 9 PAMAM dendrimer.

The multivalent effect of the dendrimers used in the devices and methods of the present invention are described in detail in PCT Publication No. WO2010/124227 and US Patent Publication No. 20120077246, which are incorporated by reference herein in their entirety.

EXAMPLES

The following examples are provided for illustration and are not in any way to limit the scope of the invention.

Example 1: Biomimetic Surface Facilitates Cell Capture

Figure 4:
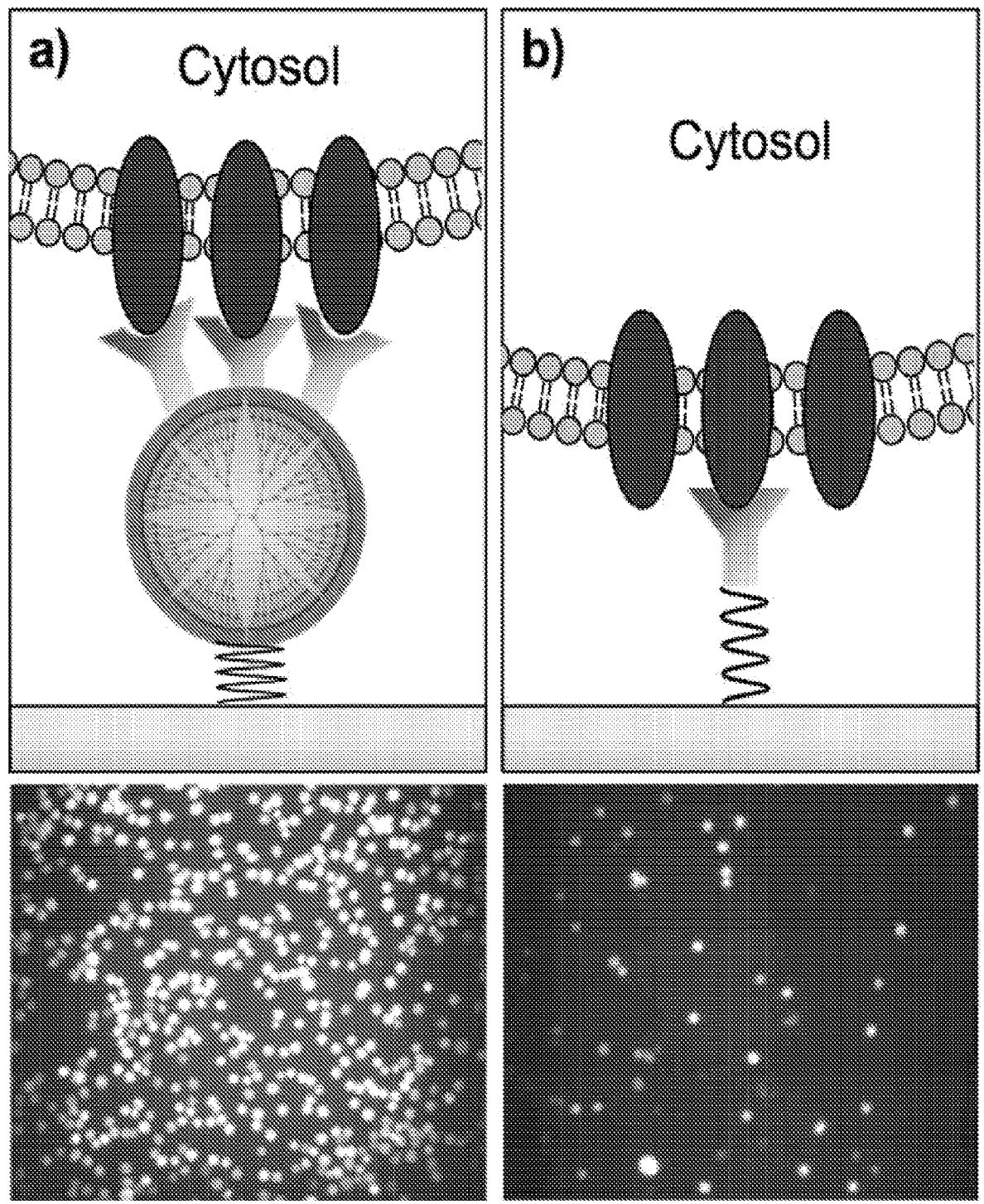
FIG. 4 shows substantially enhanced tumor cell capture on a) dendrimer-coated surface compared to b) linear polymer-immobilized surface, under identical conditions.

The novel biofunctional surfaces were prepared with immobilized selectins and aEpCAM to induce tumor cell rolling and stationary binding on these surfaces as described in Myung et al., *Langmuir* 26(11): 8589-96, 2010, which is incorporated by reference herein in its entirety. Induction of cell rolling improves capturing efficiency, which translates into higher sensitivity of this CTC device as described in Myung et al., *Langmuir* 26(11): 8589-96, 2010. Another unique feature of this device is application of nanotechnology to cell capturing. enhanced binding avidity in cancer cell targeting through the dendrimer-mediated multivalent effect (Hong et al. *J. Chem Biol.* 14(1):107-15, 2006) may significantly improve detection of the rare CTCs. To create a highly sensitive surface utilizing the multivalent effect, generation 7 (G7) poly(amidoamine) (PAMAM) dendrimers and aEpCAM were used as illustrated in FIG. 4. G7 PAMAM dendrimers were chosen due to their adequate size (8-10 nm in diameter) and number of surface functional groups (512 theoretically) to accommodate multiple aEp-CAM (around 5.5 nm in diameter of Fc region) per dendrimer, thereby enabling multivalent binding. The surface plasmon resonance (SPR) assay using BIAcore X revealed that dendrimers conjugated with ~5 aEpCAM molecules show dramatically lower KD values (stronger binding) than free aEpCAM by over a million-fold.

Figure 5A:
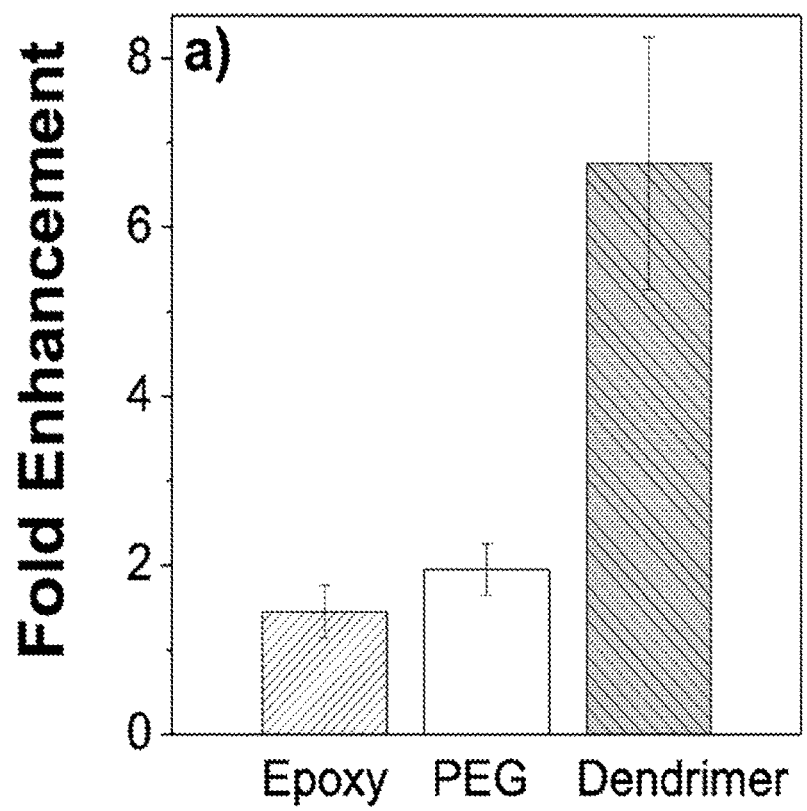
FIG. 5 demonstrates enhanced cell capture and efficiency by combination of multivalent binding and cell rolling under flow. Panel a) shows dendrimer-coated surface along with E-selectin shows ~7-fold increase in capture efficiency. Panel b) shows dendrimer surface achieves >75% tumor cell capture when MDA-MB-231 cells (10-1,000) were spiked into $10^7$ HL-60 cells. Error bars: standard error (n=3). *indicates p<0.05.
Figure 5B:
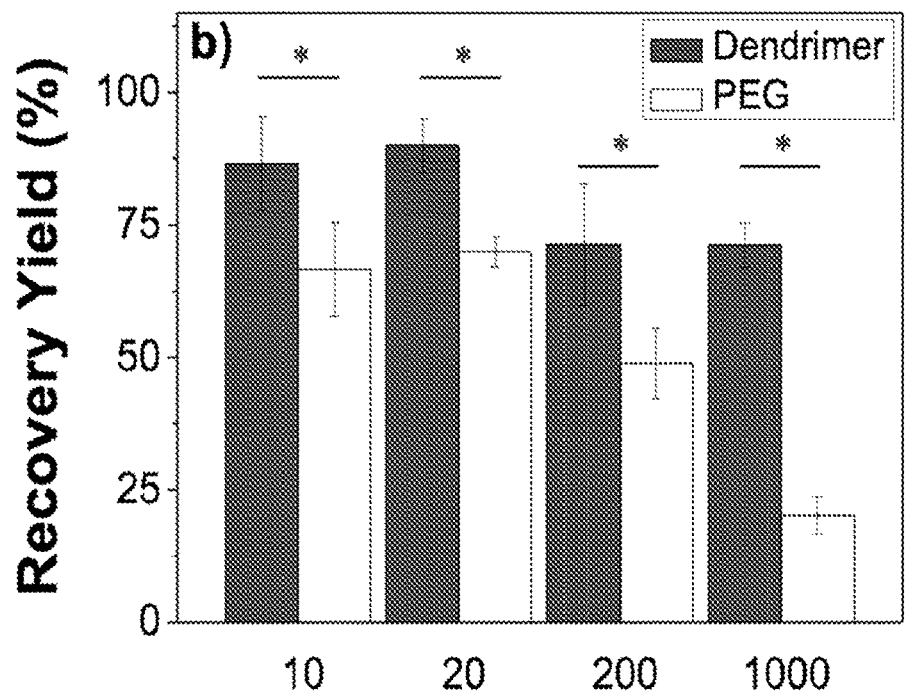

Effect of the strong multivalent binding via dendrimers was then tested on tumor cell capture surfaces, employing multiple cancer cell lines such as MDA-MB-361, MCF-7, and MDA-MB-231 cells as described in Myung et al., *Agnew Chem Int Ed Eng* 50(49):11769-72, 2011. As shown in FIG. 5a, the dendrimer-immobilized surfaces captured substantially more cells than the linear polymer (poly(ethylene glycol) (PEG))-coated ones for all three cell lines by ~7-fold. As a preliminary study, we also spiked the three cancer cell lines were spiked into the PBS buffer solution containing HL-60 cells at 10-1,000 tumor cells per $10^7$ HL-60 cells to simulate the in vivo situation. The capture efficiency of the dendrimer-aEpCAM-coated surface, together with E-selectin, was maintained at over 75% throughout the mixture ratios tested, while the PEGylated surfaces dropped the capture efficiency to below 25% (FIG. 5b). Note that the rolling cells (HL-60) other than the captured cells can be easily detached and removed from the surface by 3 min washing with EGTA-supplemened PBS buffer, as we demonstrated earlier (Myung et al. *Analytical Chem.* 86(12):6088-94, 2014).

Example 2: Biomimetic Surface Improves Sensitivity and Detection of CTCs

Figure 6A:
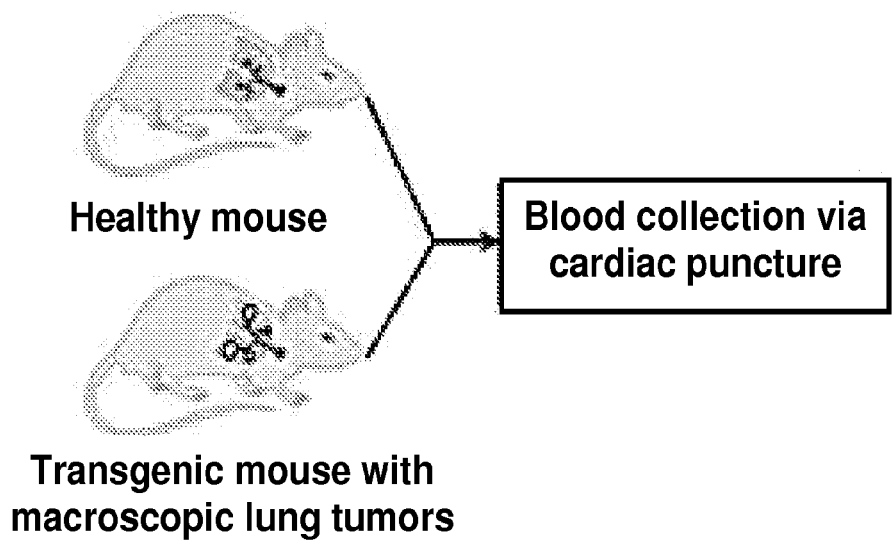
FIG. 6 shows CTC detection from healthy and transgenic mice using a single-channel flow based device with aEGFR. Panel a) shows an illustration of the experiment using healthy FVB/N mice and CEO transgenic mice. Panel b) shows comparison of the captured CTC numbers per 100 µL blood between healthy and transgenic mice. Panel c) provides immunostaining scheme of the captured cells and panel d) shows actual fluorescence images of the captured CTC after DAPI, cytokeratin, and CD45 staining.
Figure 6B:
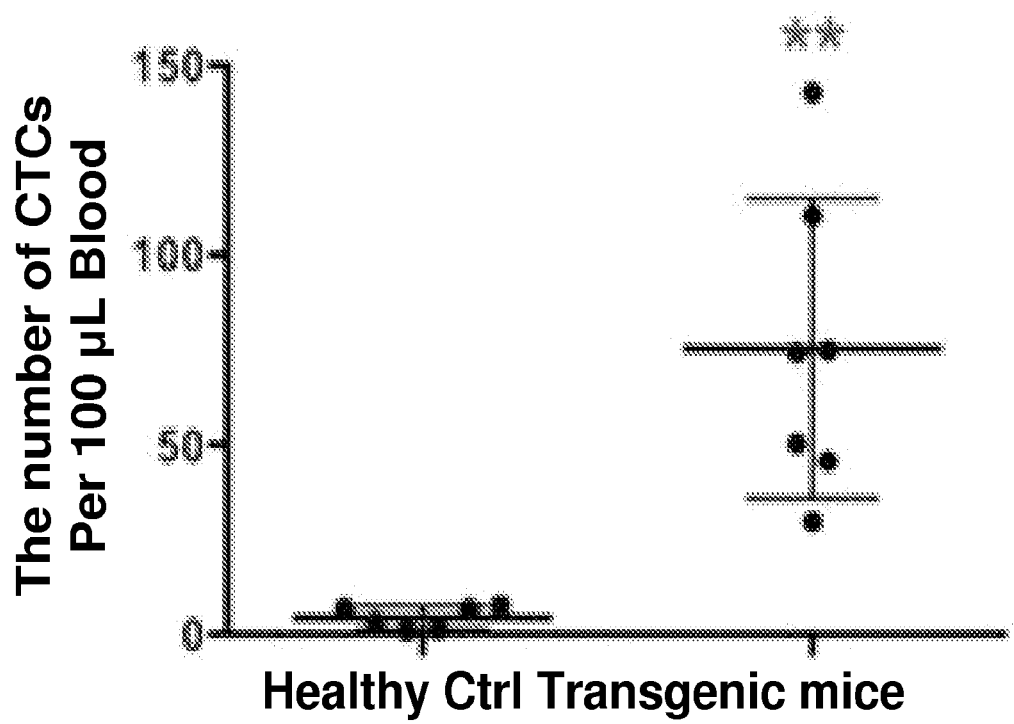
Figure 6C:
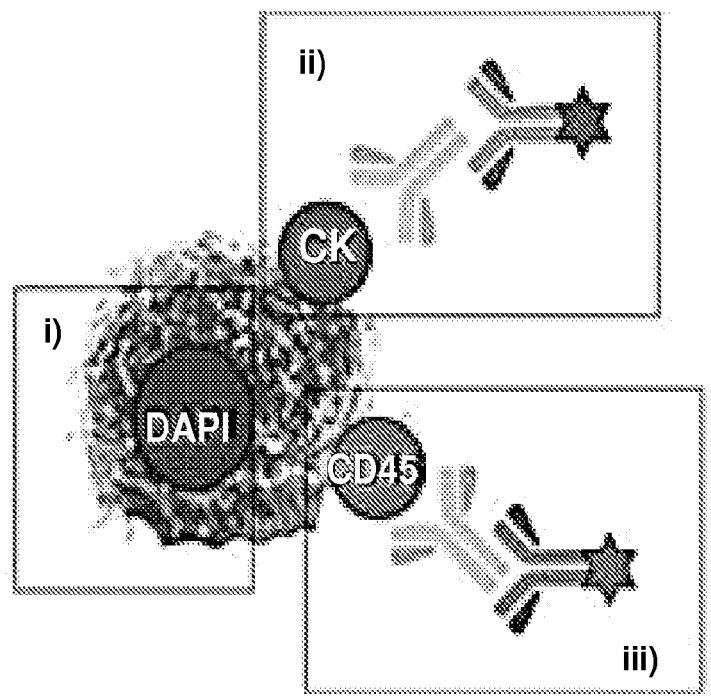
Figure 6D:
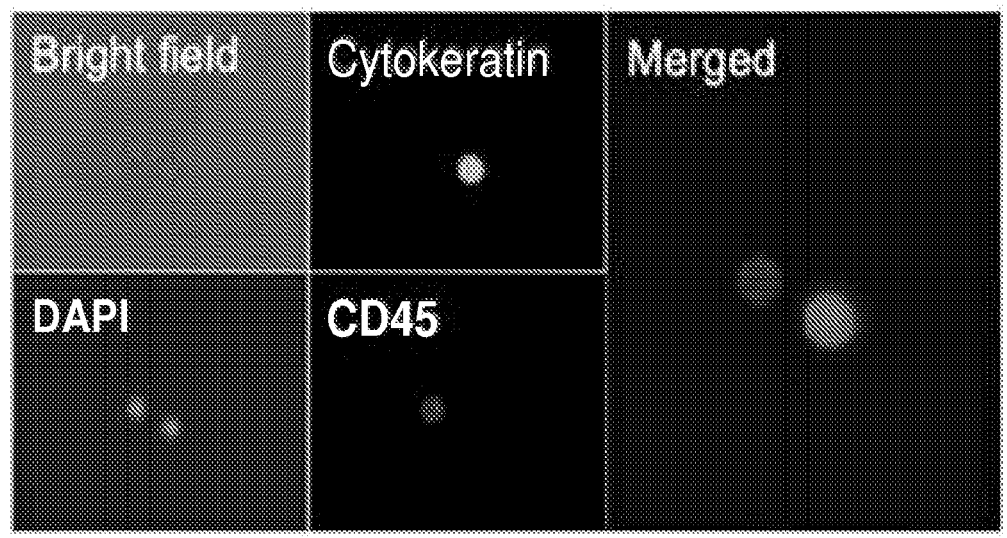

Blood samples from a transgenic mouse model for non-small cell lung cancer (NSCLC) were used to investigate the sensitivity of the biomimetic surface. The cyclin E-overexpressed (CEO) murine transgenic model of NSCLC were engineered for overexpression of the cell-cycle regulator CEO as described in Ma et al., *Proc. Natl. Acad. Sci.* 104(10):4089-96, 2013. This mouse model shows significant features found in NSCLC patients, such as chromosomal instability, pulmonary dysplasia, and hyperplasia, hedgehog-pathway activation, single and multiple adenocarcinomas, and importantly metastases. The number of CTCs captured on surface functionalized with aEGFR from healthy and transgenic mice, as shown in FIG. 6b where the transgenic mice (75.3±14.9 CTCs per 100 µL, n=7) showed a significant difference from healthy controls (4.4±1.2 CTCs per 100 µL, n=6, p=0.0011) in terms of CTC number. (mean±S.D., p<0.005). Note that CTCs were identified using a standard immunostaining method (FIGS. 7c** and *d*) as described in Nagrath et al., *Nature* 450:1235-9, 2007. Among the captured cells, cells that were bound to cytokeratin (CK) antibody (CK+), stained by DAPI (DAPI+), and yet were negative to CD45 (CD45−) were identified as CTCs. The leukocytes defined by CK−/CD45+/DAPI+ and the auto-fluorescent cells without nuclei were not counted.

The biomimetic surface was also tested for its capacity of monitoring CTC number changes as a result of therapeutic intervention. CEO mice were treated with none (control), non-specific lock nucleic acid (M47), and anti-miR-31 lock nucleic acid (M53) that is known to effective in killing NSCLC cells. Group M53 (11.3±9.2 CTCs, n=7, p=0.039) showed a significantly less CTC number compared to the M47 group (40.5±29.7 CTCs, n=6) and the control CEO mice without treatment (25.4±26.9 CTCs, n=6). Also, the data shown in FIG. 7b indicates that there is a significant difference in size between in vitro tumor cell lines (ED-1 and ED1-SC) and in vivo CTCs (control M47, and M53), demonstrating that the CTC detection method solely based on size may not be sufficiently effective. Additionally, the captured "live" in vivo CTCs could be culture expanded, as shown in FIG. 7c.

Example 3: Clinical Validation of the Biomimetic Surface

A clinical study was carried out using blood specimens collected from 20 cancer patients. The withdrawn blood collected in heparin-treated tubes (BD Vacutainer™) were kept at room temperature. The CTC capture was performed using a single chamber flow based device (shown in FIG. 7) within 24 hours after the blood-drawing. The mononuclear cells including CTCs in blood were first separated and recovered using Ficoll-Paque Plus according to the vendor's protocol. The buffy coat containing the recovered mononuclear cells were resuspended in completed DMEM media and injected into the single chamber device with aEpCAM, aEGFR, and aHER2 immobilized on the surface for CTC capture under the conditions described in Myung et al., *Analytical Chem.* 86(12):6088-94, 2014. CTCs were identified using the same method described above.

Figure 7A:
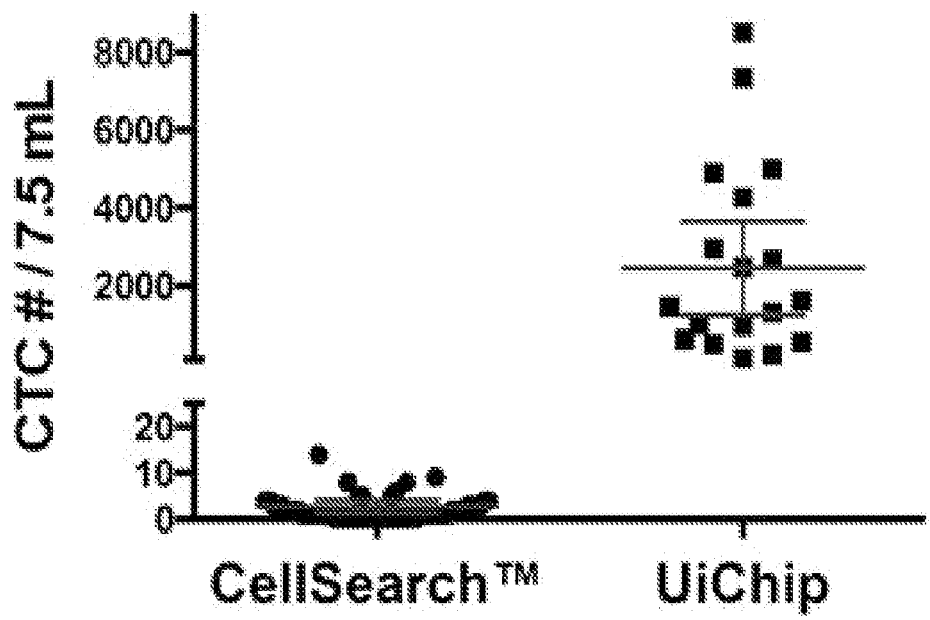
FIG. 7 provides clinical data obtained using a single-channel flow based device. Panel a) provides a comparison of numbers of CTCs per 7.5 mL of patient blood captured on CellSearch™* and the flow-based device. Panel b) demonstrates a dramatically increased CTC purity among the captured cells using the flow-based device with E-selectin for cell rolling by ~25-fold, compared to the same surface without E-selectin. *The values were obtained from the literature.
Figure 7B:
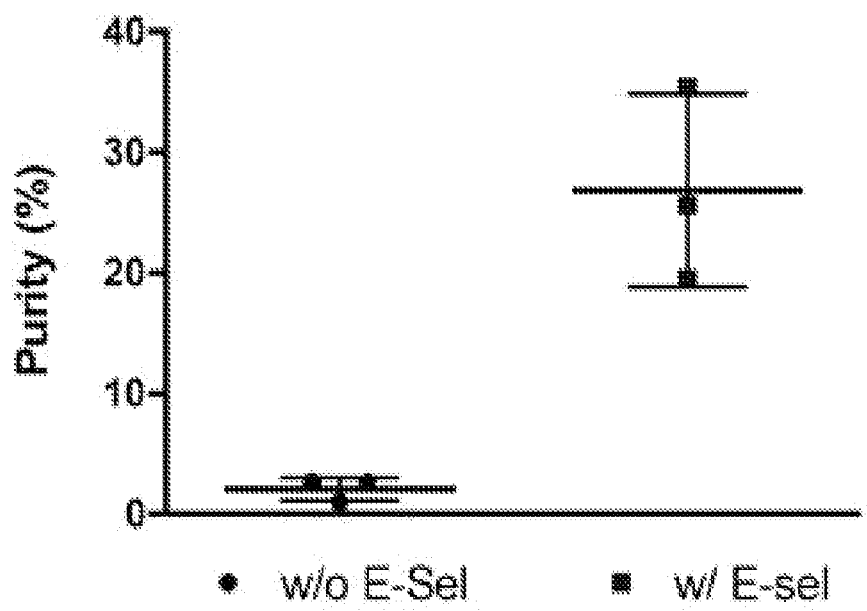

As shown in FIG. 7, the biomimetic surface demonstrated great sensitivity toward the clinical CTCs from all patients. While CellSearch™ was reported to capture only 0-46 CTCs from H&N cancer patients, the single chamber device captured on average of 2,048 CTCs per the same volume of blood (7.5 mL) (FIG. 7a). In addition, the capture surface with E-selectin exhibited a significantly enhanced CTC purity among the capture cells by ~25-fold, compared the same surface without E-selectin, indicating that the importance of cell rolling in our device determining the capture purity and specificity (FIG. 7b). In summary, the in vivo and clinical studies indicate that biomimetic surface is of great potential to be developed as a highly sensitive, specific, and cost-effective CTC detection system that effectively captures "live" clinical CTCs with potential for culture expansion.

Example 4: Preparation and Characterization of Multi-Channel Device

In this study, the multi-chamber device employed multiple antibodies specific to CTC and multiple cCSC-specific antibodies immobilized in pattern on the capture surface of the mulichamber device. The patterns contained E-selectin for rolling and G7 PAMAM dendrimers with anti-epithelial-cell-adhesion-molecule (aEpCAM), and anti-human epidermal growth factor receptor 2 (aHER2), along with aCD44, aCD10, aCD271, for multivalent capturing. Furthermore, to effectively isolate CSCs out of the capture CTCs, immobilized antibody specific for the CSC markers, such as CD44, CD10, and CD27, were also immobilized on the capture surface.

Figure 8:
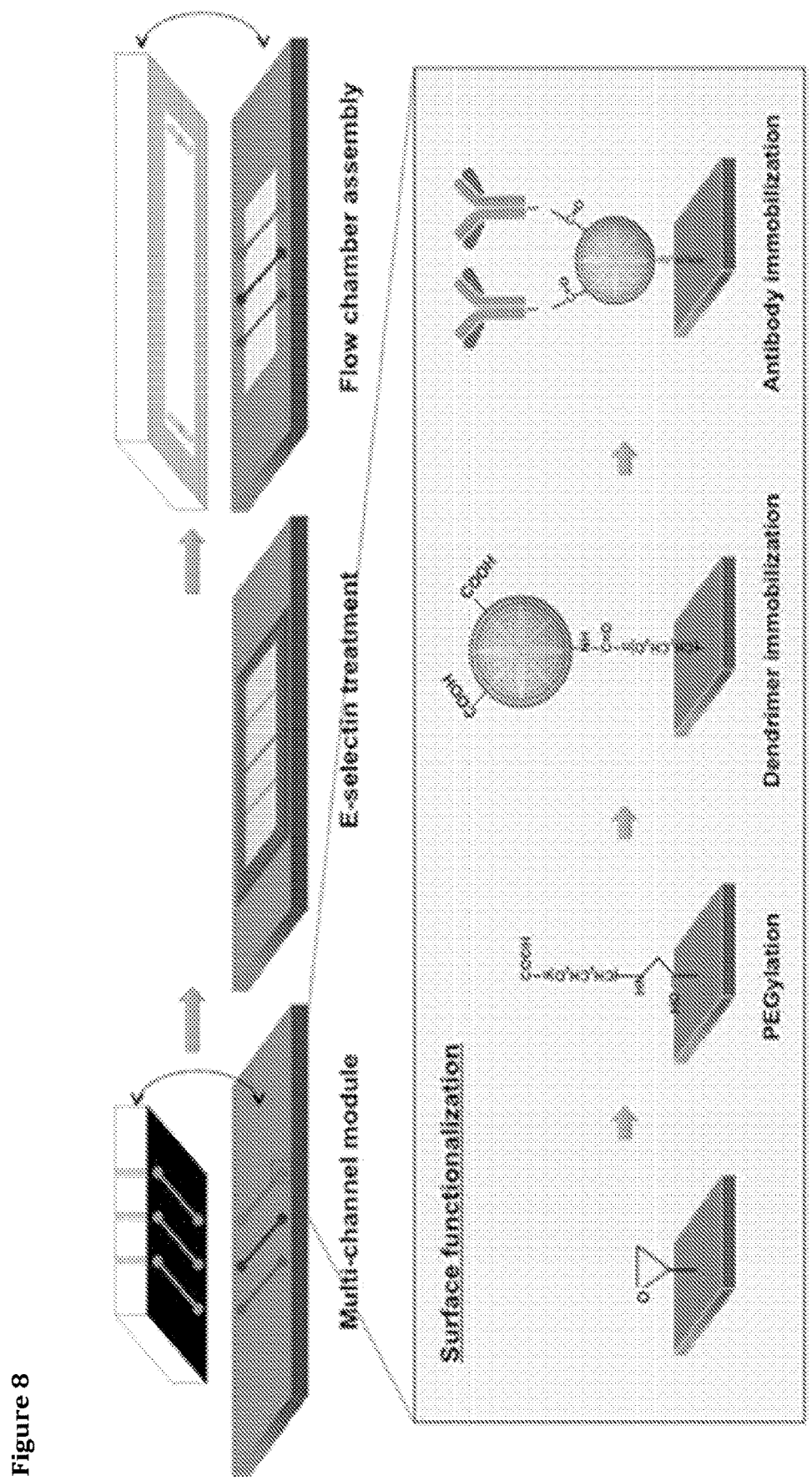
FIG. 8 provides a schematic of the surface functionalization using multiple antibodies and dendrimers.
Figure 9A:
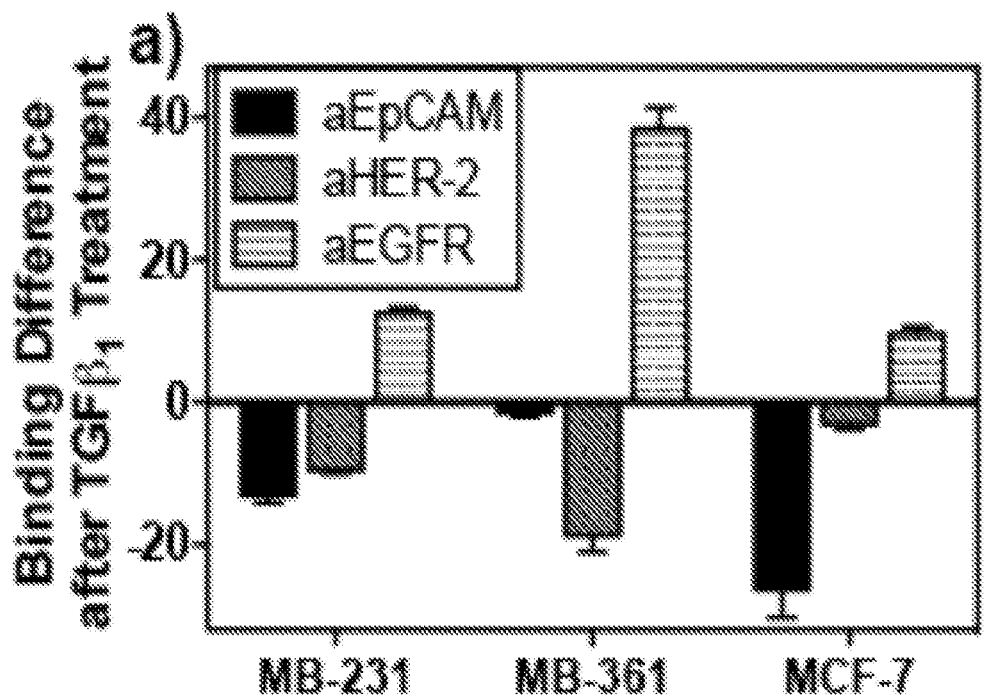
FIG. 9 demonstrates effective capture of post-EMT cells using various dendrimer-antibody conjugates. a) Receptor expression changes of three BCA cells upon EMT by TGF-β treatment. b) Fold enhancement of surface capture of MDA-MB-231 cells using dendrimer-coated surfaces before and after EMT. Error bars: standard error (n=3). *indicates p<0.05.
Figure 9B:
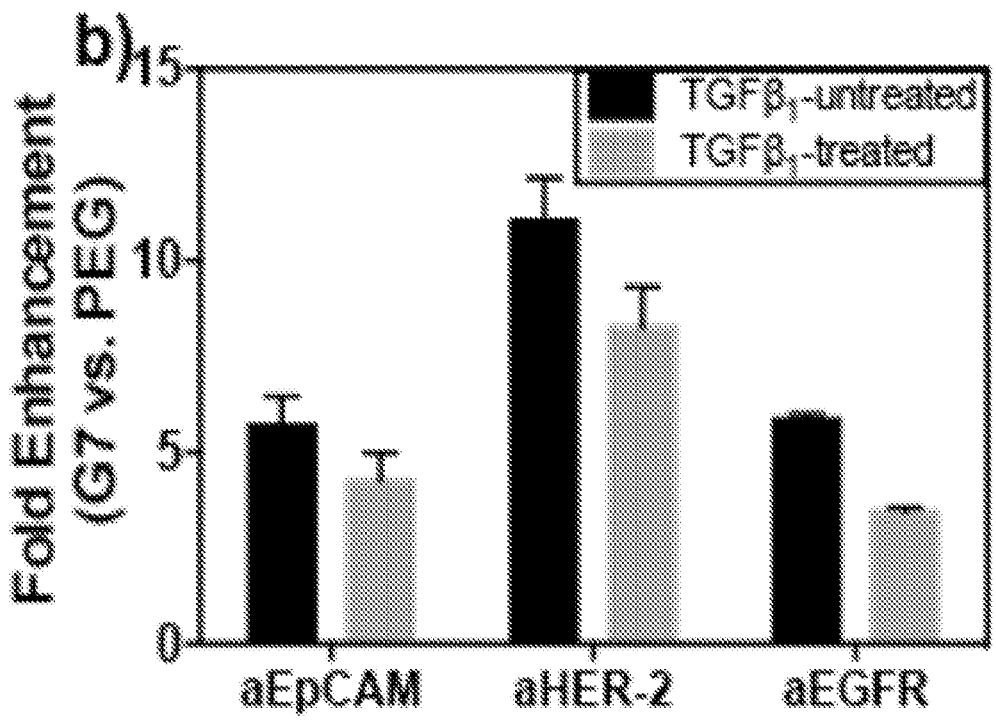
Figure 10:
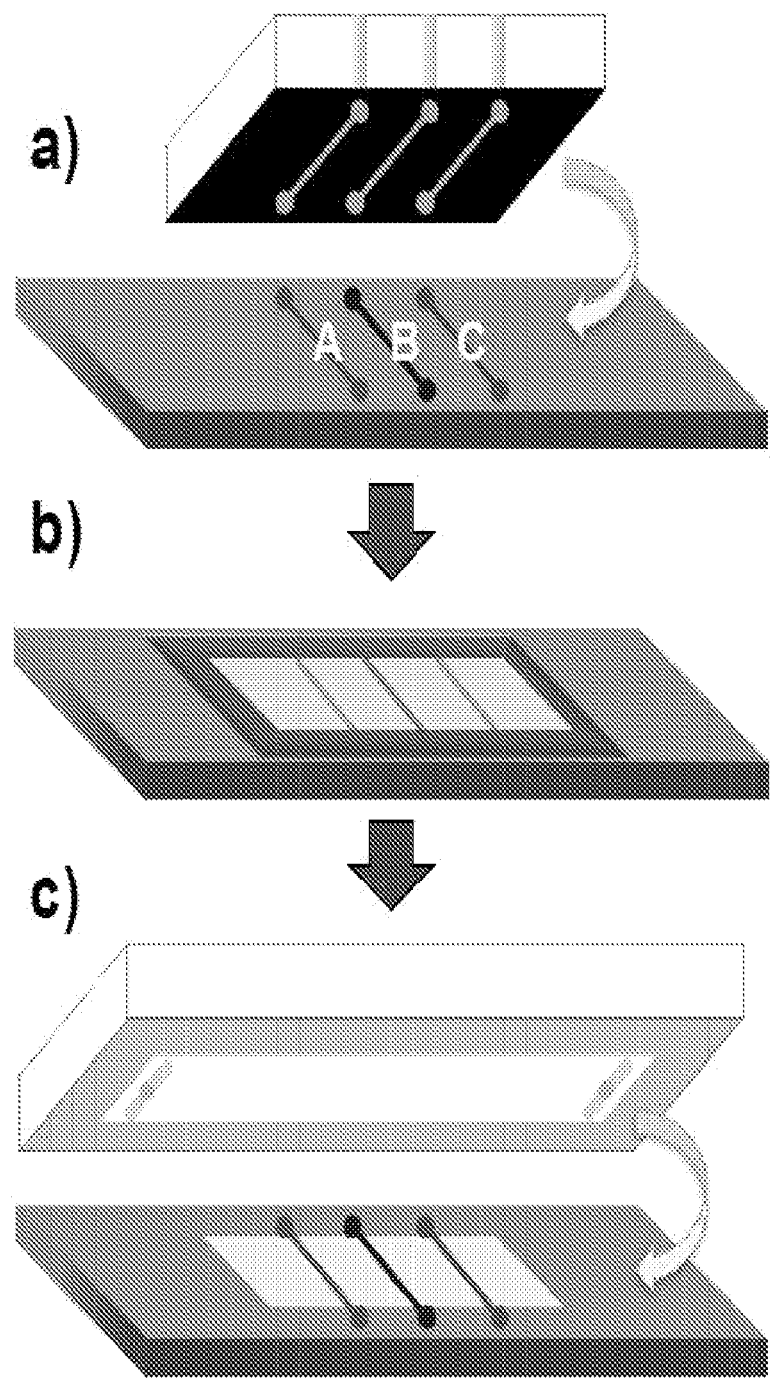
FIG. 10 shows a schematic diagram of preparation of multifunctional surfaces assembled into a flow chamber: a) apply multi-channel PDMS stencil and perfuse antibodies for surface immobilization; b) remove the stencil and back-fill E-selectin; and c) assemble with a flow chamber.

A multifunctional surface was prepared by a layer-by-layer approach. As shown in FIG. 8, an epoxy-functionalized surface was micropatterned with various antibodies by soft lithography using a mutli-channel stencil made of poly(dimethylsiloxane) (PDMS). The multi-patterned surface was then treated with E-selectin to backfill the empty space to subsequently induce rolling of various cells. The immobilization of aEpCAM, aHER2, and aEGFR was performed on top of the G7 PAMAM dendrimer-coated surfaces in a patterned manner, added with E-selectin, and assembled into a flow chamber, resulting in a biomeimetic surface using a similar immobilization protocol as described in Myung et al. *Analytical Chem.* 86(12):6088-94, 2014. The protein immobilization was confirmed using fluorescent antibodies such as E-selectin antibody/FITC conjugate and fluorescence tagged antibodies. To ensure that the proteins were covalently immobilized, the surface was re-imaged after the thorough rinsing steps using buffers with high ionic strength as described in Hong et al., *Langmuir* 23(24) 12261p-8, 2007. Additionally, X-ray Photoelectron Spectroscopy was used to analyze the elemental compositions of the surfaces To confirm that the biomimetic surface effectively captured the tumor cells with highly heterogeneous phenotypes, the 5 cell lines were induced to undergo EMT and perfused into the device. Briefly, the head and neck cancer cells were treated with TGF-β at concentrations of 10 and 20 ng/mL for 72 hrs. The EMT was confirmed by western-blotting as well as by observing the enhanced cytoskeletal activities using both pico-to-nano-scale AFM force measurements and cell-level wound healing assay, as described in Lee et al., 117(31): 9233-40, 2013. The capture efficiencies and the surface behaviors of the post-EMT cells were compared to the pre-EMT counterparts using the similar method described in Myung et al., *Agnew Chem Int Ed Eng* 50(49): 11769-72, 2011. (see FIG. 9)

In vitro flow chamber tests using the 5 cell lines are performed to optimize the pattern dimensions. The lengths and angles of the protein patterns are optimized to stably induce rolling and to maximize tumor cell-specific capturing. Lengths of E-selectin and dendrimer-antibodies domains are optimized to a condition where the two domains induce stable rolling of cells (1-10 μm/s) at various shear stresses of 0.5-4.0 dyn/cm$^2$ and maximize the number of captured cells per surface area, respectively. The same optimization process is also performed using the cells after being spiked into human blood obtained from healthy donors.

Quantitative measurements of dissociation constants ($K_D$) are obtained for the interaction of surface-immobilized dendrimer-antibody conjugates with cell-mimicking microspheres using SPR as described in Myung et al. *Analytical Chem.* 83(3):1078-83, 2011. For example, an EpCAM fragment is biotinylated using the biotinylation kit, followed by conjugation with microbead-streptavidin conjugates. Based on the kinetic parameters, an optimal number of surface-immobilized antibodies per dendrimer are determined. The optimized device is validated and examined in its efficiency in capturing a series of CTC.

Figure 11:
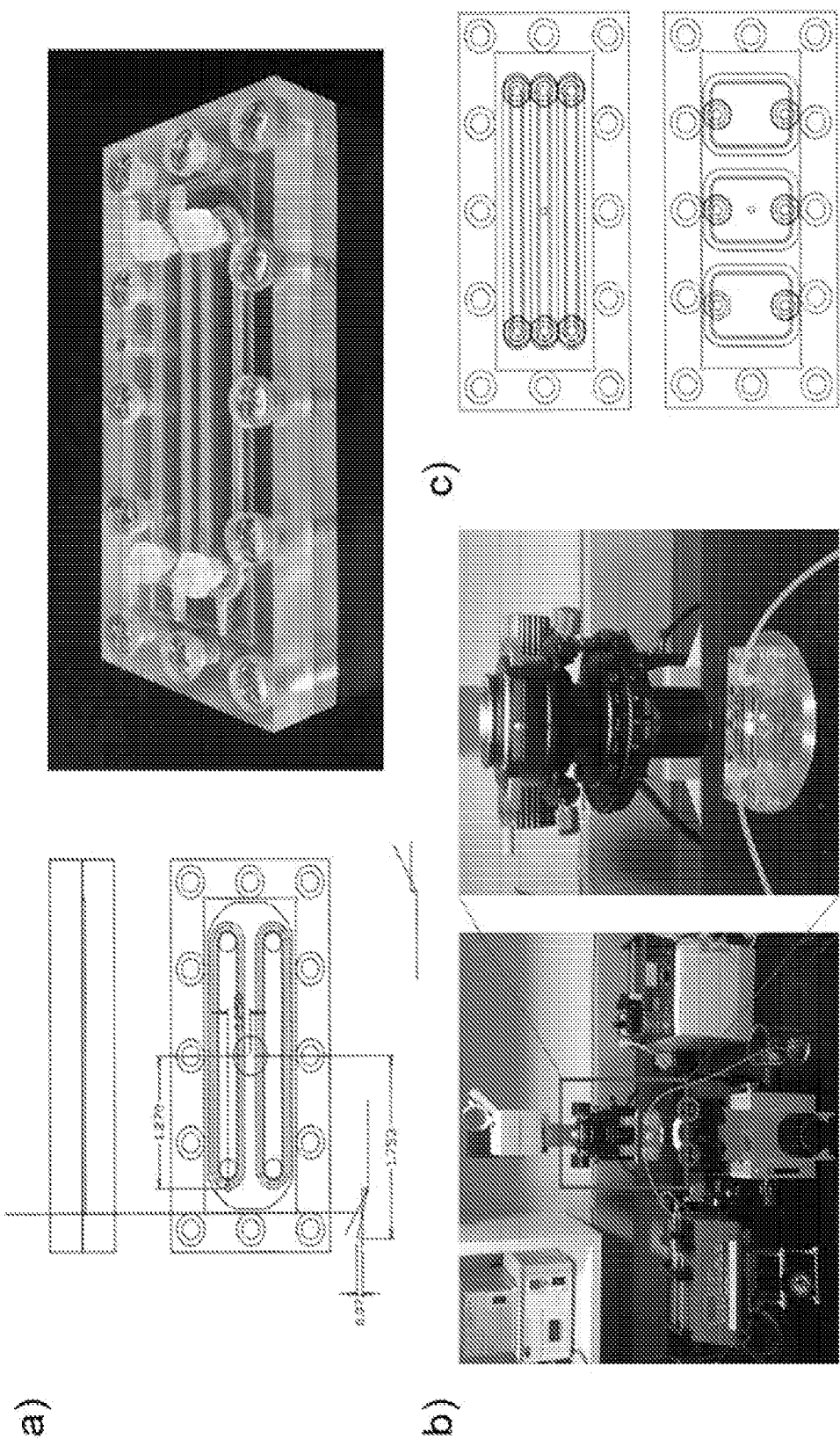
FIG. 11 shows customized flow chambers with various channels. Panel a) provides a two channel-flow chamber device. Panel b) shows the multichannel flow based device assembled with a functionalized capture surface mounted on a fluorescence microscope. Panel c) provides additional designs of flow based devices with three channels.

Example 6: Fabrication of Multi-Channeled Device for High Throuput and Efficient Capture The optimized patterned surfaces described above were translated into a multichannel device. A series of custom-designed flow chamber with 2-3 channels were fabricated with a longer channel length, which increase the capture efficiency, throughput, and differential detection of CTCs and CSCs. The multi-channel flow chamber (some channel designs and the set up with a microscope are shown in FIG. 11) provides more flexibility in surface patterning and enhanced sensitivity than the commercially available single-channel flow chamber (Glycotech), without a major configurational change from the system that is currently being used in the lab.

The prototype designs are compared in their capture efficiencies using various tumor cells spiked into human blood from healthy donors. The comparison experiments are performed at a concentration (20-2,000 tumor cells spiked into 1 mL of human blood) and for the same capture time (10 min).

What is claimed:

1. A microfluidic device for capturing a Circulating Tumor Cell (CTC) and a Circulating Cancer Stem Cell (CSC) from a sample, comprising:
   (a) a first channel comprising a cell capture surface and a flow mobilization surface, wherein a CTC-specific or CSC-specific capturing agent and a cell rolling-inducing agent are immobilized to the cell capture surface, wherein the capturing agent is immobilized via a modified poly(amidoamine) dendrimer covalently attached to the cell capture surface agent;
   (b) a second channel comprising a cell capture surface and a flow modification surface, wherein a CSC-specific or CTC-specific capturing agent and a cell rolling-inducing agent are immobilized to the cell capture surface, wherein the capturing agent is immobilized via a modified poly(amidoamine) dendrimer covalently attached to the cell capture surface agent and wherein the cell rolling-inducing agent is E-selectin or a CTC binding fragment of E-selectin.

2. The device of claim 1, wherein the first and second channels are connected.

3. The device of claim 1, wherein each channel has an inlet and an outlet.

4. The device of claim 1, wherein the capturing agent is an antibody, an antibody fragment, an engineered antibody, folic acid, transferrin, a peptide, and an aptamer.

5. The device of claim 1, wherein the capturing agent specific for CTC specifically binds a moiety on a CTC surface.

6. The device of claim 5 wherein the capturing agent is an RGD peptide.

7. The device of claim 1 wherein the capturing agent specific for CSC specifically binds a moiety on a CSC surface.

8. The device claim 1, wherein the capturing agent is immobilized to the cell capture surface by direct attachment to the cell capture surface.

9. The device of claim 1, wherein the capturing agent is immobilized on cell capture surface by attachment to a linker directly attached to the surface.

10. The device of claim 9, wherein the linker is a polymeric nanolinker.

11. The device of claim 10, wherein the polymeric nanolinker comprises a modified poly(amidoamine) dendrimer covalently attached to polyethylene glycol.

12. The device of claim 10, wherein the polymeric nanolinker comprises polyester-n-carboxylate-1-alkyne dendron covalently attached to polyethylene glycol, wherein n is 8, 16, 32, 64, or 128.

13. The device of claim 1, wherein the cell rolling-inducing agent and the capturing agent are arranged in a substantially uniform manner.

14. The device of claim 13, wherein the cell capture surface of the first channel or the second channel comprises a pattern of first and second regions, the first region comprising the cell rolling-inducing agent, and the second region comprising the capture agent.

15. The device of claim 14, wherein the first region further comprises the capture agent.

16. The device of claim 14, wherein the first and second regions are arranged in an alternating pattern.

17. The device of claim 13, wherein the cell capture surface of both the first channel or the second channel comprise a pattern of first and second regions, the first region comprising the cell rolling-inducing agent, and the second region comprising the capture agent.

18. The device of claim 1, wherein the cell-rolling inducing agent is covalently attached to the cell capture surface.

19. The device of claim 1, wherein the cell-rolling inducing agent is immobilized to a surface of the microfluidic device via a linker.

20. A method of capturing a Circulating Tumor Cell (CTC) and Circulating Cancer Stem Cell (CSC) from a sample comprising the step of introducing said sample into the device of claim 1.

* * * * *